United States Patent
Saito et al.

(10) Patent No.: US 7,004,980 B2
(45) Date of Patent: Feb. 28, 2006

(54) HAIR DYE COMPOSITION

(75) Inventors: Yoshinori Saito, Tokyo (JP); Kenzo Koike, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/494,729

(22) PCT Filed: Nov. 6, 2002

(86) PCT No.: PCT/JP02/11564

§ 371 (c)(1),
(2), (4) Date: May 6, 2004

(87) PCT Pub. No.: WO03/039501

PCT Pub. Date: May 15, 2003

(65) Prior Publication Data

US 2004/0255398 A1    Dec. 23, 2004

(30) Foreign Application Priority Data

Nov. 7, 2001   (JP) .............................. 2001-341853

(51) Int. Cl.
*A61K 7/13*   (2006.01)
(52) U.S. Cl. ...................... 8/405; 8/406; 8/409; 8/435; 8/611; 8/619; 8/620
(58) Field of Classification Search .................... 8/405, 8/406, 409, 435, 611, 619, 620
See application file for complete search history.

(56) References Cited

U.S. PATENT DOCUMENTS

| 3,796,723 A | 3/1974 | Kaiser et al. .......... 260/326.11 |
| 5,346,509 A | 9/1994 | Schultz et al. ................. 8/423 |
| 5,556,989 A * | 9/1996 | Lagrange et al. ........... 548/491 |
| 6,371,993 B1 * | 4/2002 | Moeller et al. ................ 8/407 |

FOREIGN PATENT DOCUMENTS

| JP | 1-233210 | 9/1989 |
| WO | WO 99/66890 | 12/1999 |
| WO | 01/93818 | 12/2001 |

OTHER PUBLICATIONS

DataBase CA—Chemical Abstract Service—XP 002338135.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

Provided is a one-part air-oxidative hair dye composition containing (A) 5,6-dihydroxyindoline-2-carboxylic acid or a salt thereof, (B) an alkali agent selected from sodium hydroxide, potassium hydroxide, ammonia, guanidine, basic amino acids and carbonates, and (C) from 10 to 50 wt. % of a water compatible organic solvent, said composition being substantially free of an alkanolamine, and having a pH of from 8 to 12.

This one-part air-oxidative hair dye composition has excellent hair dyeing power.

19 Claims, No Drawings

HAIR DYE COMPOSITION

TECHNICAL FIELD

The present invention relates to a one-part air-oxidative hair dye composition having excellent dyeing properties.

BACKGROUND ART

It is known that 5,6-dihydroxyindoline-2-carboxylic acid or a salt thereof is converted into a melanin pigment by the oxygen in the air. This knowledge is utilized for air-oxidative hair dye compositions. The above-described substance however does not have sufficient dyeing properties.

DISCLOSURE OF THE INVENTION

An object of the present invention is therefore to improve the dyeing performance of an air-oxidative hair dye composition containing 5,6-dihydroxyindoline-2-carboxylic acid or a salt thereof.

The present inventors have found that excellent dyeing properties can be achieved by incorporating a predetermined amount of a water-compatible organic solvent in an air-oxidative hair dye composition containing 5,6-dihydroxyindoline-2-carboxylic acid or a salt thereof, using a specific compound as an alkali agent, and adjusting the pH of the composition to 8 or greater.

According to the present invention, there is thus provided a one-part air-oxidative hair dye composition which contains (A) 5,6-dihydroxyindoline-2-carboxylic acid or a salt thereof, (B) an alkali agent selected from sodium hydroxide, potassium hydroxide, ammonia, guanidine, basic amino acids and carbonate salts, and (C) from 10 to 50 wt. % of a water-compatible organic solvent, said composition being substantially free of an alkanolamine, and having a pH of from 8 to 12.

BEST MODE FOR CARRYING OUT THE INVENTION

As the 5,6-dihydroxyindoline-2-carboxylic acid or a salt thereof serving as Component (A), 5,6-dihydroxyindoline-2-carboxylic acid or its hydrochloride, hydrobromide, sulfate, phosphate, acetate, propionate, lactate or citrate can be used. It is also possible to incorporate 1-acyl-5,6-diacyloxyindoline-2-carboxylic acid, or 5,6-diacyloxyindoline-2-carboxylic acid, or a carboxylic acid ester thereof in a hair dye composition and then hydrolyze it under basic conditions to produce 5,6-dihydroxyindoline-2-carboxylic acid.

The above-described 5,6-dihydroxyindoline-2-carboxylic acid and salts thereof may be used either singly or in combination of two or more, and its or their amount is preferably from 0.01 to 10 wt. %, more preferably from 0.05 to 5 wt. % based on the whole composition.

The alkali agent serving as Component (B) is selected from sodium hydroxide, potassium hydroxide, ammonia, guanidine, basic amino acids and carbonates. Specific examples of the carbonates include sodium carbonate, potassium carbonate, guanidine carbonate and sodium bicarbonate. The dyeing properties of 5,6-dihydroxyindoline-2-carboxylic acid or a salt thereof are deteriorated by an alkanolamine so that the alkali agent is substantially free of an alkanolamine. The term "substantially free" as used herein means that the amount is small enough not to cause any adverse effects on the dyeing properties. More specifically, the amount of an alkanolamine is preferably 1 wt. % or less, more preferably 0.2 wt. % or less, even more preferably 0 wt. %, based on the whole composition.

The alkali agents may be used either singly or in combination of two or more and its or their amount is preferably from 0.01 to 20 wt. %, more preferably from 0.1 to 10 wt. % based on the whole composition.

Examples of the water-compatible organic solvent serving as Component (C) include lower alcohols such as ethanol and propanol; glycols such as ethylene glycol and propylene glycol; ethylene glycol monoethers such as ethylene glycol monomethyl ether, ethylene glycol monoethyl ether and ethylene glycol monobutyl ether; carbitols such as diethylene glycol monoethyl ether and diethylene glycol monobutyl ether; and aromatic alcohols such as benzyloxyethanol and benzyl alcohol. Of these, the lower alcohols and glycols are preferred. When an aromatic alcohol such as benzyloxyethanol or benzyl alcohol is used, combined use with another solvent, especially with a lower alcohol or glycol is preferred.

The water-compatible organic solvents may be used either singly or in combination of two or more and its or their amount may range from 10 to 50 wt. % in view of dyeing properties, of which from 15 to 45 wt. % is preferred, with from 20 to 40 wt. % being more preferred.

Under basic conditions, 5,6-dihydroxyindoline-2-carboxylic acid or a salt thereof reacts with the oxygen in the air and is converted into a melanin pigment. The pH of the hair dye composition of the present invention is therefore controlled to fall within a range of from 8 to 12, preferably from 8.5 to 10.5, more preferably from 9 to 10.5 in order to prevent scalp irritation while maintaining a high hair dyeing power.

As the pH regulator, an inorganic or organic acid such as hydrochloric acid, sulfuric acid, phosphoric acid, citric acid or lactic acid can be used as needed, as well as the alkali agent serving as Component (B).

The hair dye composition of the present invention may be supplied in the form of a cream, gel, lotion, foam and the like. In view of stability, it is preferably packaged in the form of an aerosol. When the composition is used as a gradual dyeing type, it is possible to diminish the appearance of gray hair little by little without being noticed by others, by applying the hair dye composition to the hair, allowing it to stand for 1 to 10 minutes and repeating this operation from two to several times.

In addition to the above-described essential components, components ordinarily employed for hair dye agents, for example, surfactant, thickener, stabilizer, buffer, perfume, component/material for improving the feel of the hair, chelating agent, solubilizing agent, and antiseptic may be incorporated in the hair dye composition of the present invention as needed, depending on the purpose of use. When the composition is provided in an aerosol form, a propellant such as compressed gas (nitrogen gas, carbon dioxide gas, argon gas, etc.) or liquefied gas (liquefied petroleum gas, lower saturated hydrocarbon, dimethyl ether, etc.) may be filled in a pressure tight container (aerosol can, etc.).

EXAMPLES

In the below-described examples and comparative examples, the dyeing power was evaluated by a difference ($\Delta E$) in the color of a dyed tress measured by a spectrophotometer ("CM-2002", product of Minolta). The difference was calculated in accordance with the below-described equation:

$$\Delta E = \{(L_1-L_0)^2 + (a_1-a_0)^2 + (b_1-b_0)^2\}^{1/2}$$

($L_0, a_0, b_0$): the color of a goat hair tress before dyeing
($L_1, a_1, b_1$): the color of a goat hair tress after dyeing

Example 1 and Comparative Example 1

The dye solutions as shown in Table 1 were prepared. These dye solutions were each applied to 1 g of goat hair and the hair was dyed at 30° C. for 15 minutes. The dyed hair was then washed with water, shampooed, rinsed and dried. The color difference (ΔE) before and after dyeing is shown in Table 1.

TABLE 1

| Composition (wt. %) | Example 1 | Comp. Ex. 1 | Comp. Ex. 2 |
| --- | --- | --- | --- |
| 5,6-Dihydroxyindoline-2-carboxylic acid hydrochloride | 1 | 1 | 1 |
| 28 wt. % Aqueous ammonia | 3 | 3 | 3 |
| Ethanol | 30 | 30 | — |
| 10 wt. % Sulfuric acid | Amount enough to regulate pH | Amount enough to regulate pH | Amount enough to regulate pH |
| Water | Balance | Balance | Balance |
| pH | 9 | 7 | 9 |
| Color difference (ΔE) between before and after dyeing | 36 | 18 | 30 |

Examples 2 to 7

Compositions of Examples 2 to 7 shown in Table 2 were used as a stock solution and, with a propellant (LPG), each composition was filled in an aerosol container (stock solution:propellant=90:10, weight ratio).

To the gray hair tress, 1 g (in terms of the stock solution) of each of the aerosol type hair dyes prepared using the compositions of Examples 2 to 7 was applied and the tress was dyed at 30° C. for 5 minutes. The dyed tress was then washed with water, shampooed, rinsed and dried. This operation was repeated every 7 days (week), 5 times in total. The color difference (ΔE) between before and after dyeing is shown in Table 2.

TABLE 2

| | Examples | | | | | |
| --- | --- | --- | --- | --- | --- | --- |
| Composition (wt. %) | 2 | 3 | 4 | 5 | 6 | 7 |
| 5,6-Dihydroxyindoline-2-carboxylic acid hydrochloride | 0.45 | 0.45 | 0.45 | 0.45 | 0.45 | 0.45 |
| Guanidine carbonate | 1.4 | — | — | 0.7 | — | — |
| Sodium carbonate | — | 0.8 | — | 0.4 | — | 0.4 |
| Potassium carbonate | — | — | 1.0 | — | — | — |
| Arginine | — | — | — | — | 2.8 | — |
| Sodium hydroxide | — | — | — | — | — | 0.7 |
| Ethanol | 30 | 30 | 20 | 30 | 30 | 30 |
| Benzyloxyethanol | — | — | 5 | — | — | — |
| Softanol 90 | 0.1 | 0.1 | 0.1 | 0.1 | 0.1 | 0.1 |
| Xanthan gum | 1 | 1 | 1 | 1 | 1 | 1 |
| 10 wt. % Sulfuric acid | Amount enough to regulate pH | Amount enough to regulate pH | Amount enough to regulate pH | Amount enough to regulate pH | Amount enough to regulate pH | Amount enough to regulate pH |
| Water | Balance | Balance | Balance | Balance | Balance | Balance |
| pH | 10 | 9 | 9 | 8 | 8 | 8.5 |
| Color difference (ΔE) between before and after dyeing | 41 | 40 | 39 | 38 | 36 | 37 |

The invention claimed is:

1. A one-part air-oxidative hair dye composition, comprising:
   (A) 5,6-dihydroxyindoline-2-carboxylic acid or a salt thereof,
   (B) an alkali agent selected from the group consisting of sodium hydroxide, potassium hydroxide, ammonia, guanidine, a basic amino acid, a carbonate, and mixtures thereof, and
   (C) from 10 to 50 wt. % of a water-compatible organic solvent,
   said composition being substantially free of an alkanolamine, and having a pH of from 8 to 12.

2. The composition according to claim 1, comprising from 0.01 to 10 wt. % of component (A).

3. The composition according to claim 1, comprising from 0.01 to 20 wt. % of component (B).

4. The composition according to claim 1, wherein the water-compatible organic solvent is selected from the group consisting of lower alcohols, glycols, ethylene glycol monoethers, carbitols, aromatic alcohols, and mixtures thereof.

5. The composition according to claim 1, wherein the pH is from 8.5 to 10.5.

6. The composition according to claim 1, further comprising a pH regulator.

7. The composition according to claim 1, wherein the composition is in an aerosol form and further comprises a propellant.

8. The composition according to claim 1, wherein said salt of 5,6-dihydroxyindoline-2-carboxylic acid is a hydrochloride, hydrobromide, sulfate, phosphate, acetate, propionate, lactate or citrate.

9. The composition according to claim 1, wherein said component (B) is selected from the group consisting of sodium carbonate, potassium carbonate, guanidine carbonate, sodium bicarbonate and mixtures thereof.

10. The composition according to claim 1, wherein said component (A) is present in an amount of from 0.05 to 5 wt. % based on the total amount of the composition.

11. The composition according to claim 1, wherein an amount of said alkanolamine is 1 wt. % or less, based on the total amount of the composition.

12. The composition according to claim 1, wherein an amount of said alkanolamine is 0.2 wt. % or less, based on the total amount of the composition.

13. The composition according to claim 1, wherein an amount of said alkanolamine is 0 wt. %, based on the total amount of the composition.

14. The composition according to claim 1, wherein said component (B) is present in an amount of from 0.1 to 10 wt. %, based on the total amount of the composition.

15. The composition according to claim 1, wherein said water compatible solvent is a lower alcohol.

16. The composition according to claim 1, wherein said water compatible solvent is glycol.

17. The composition according to claim 1, wherein said an amount of said water compatible solvent is 15 to 45 wt. %, based on the total amount of the composition.

18. The composition according to claim 1, wherein said an amount of said water compatible solvent is 20 to 40 wt. %, based on the total amount of the composition.

19. The composition according to claim 1, wherein said pH is 9 to 10.5.

* * * * *